(12) United States Patent
Auguste et al.

(10) Patent No.: US 7,183,351 B2
(45) Date of Patent: *Feb. 27, 2007

(54) HYDROPHILIC ADHESIVE COMPOSITIONS

(75) Inventors: Stephane Auguste, Varois et Chaignot (FR); Nadege Desmaison, Dijon (FR)

(73) Assignee: Laboratoires Urgo, Chenove (FR)

( * ) Notice: Subject to any disclaimer, the term of this patent is extended or adjusted under 35 U.S.C. 154(b) by 0 days.

This patent is subject to a terminal disclaimer.

(21) Appl. No.: 10/514,259

(22) PCT Filed: Apr. 16, 2003

(86) PCT No.: PCT/FR03/01210

§ 371 (c)(1),
(2), (4) Date: Oct. 15, 2004

(87) PCT Pub. No.: WO03/087254

PCT Pub. Date: Oct. 23, 2003

(65) Prior Publication Data

US 2005/0228115 A1 Oct. 13, 2005

(30) Foreign Application Priority Data

Apr. 17, 2002 (FR) .................. 02 04779

(51) Int. Cl.
C08F 290/04 (2006.01)
C08F 51/00 (2006.01)
C08K 53/00 (2006.01)
C09J 7/02 (2006.01)

(52) U.S. Cl. ............... 524/504; 524/505; 524/517; 523/105; 523/111

(58) Field of Classification Search ........... 523/105, 523/111; 524/504, 505, 517
See application file for complete search history.

(56) References Cited

U.S. PATENT DOCUMENTS

| 4,369,284 A | 1/1983 | Chen |
| H1022 H | 2/1992 | Holden et al. ............ 524/474 |
| 5,122,569 A | 6/1992 | Scheibelhoffer et al. |
| 5,167,649 A | 12/1992 | Zook |
| 5,552,495 A | 9/1996 | Miller et al. |
| 6,576,712 B2 * | 6/2003 | Feldstein et al. ......... 525/326.9 |
| 2004/0148003 A1 | 7/2004 | Udipi et al. |

FOREIGN PATENT DOCUMENTS

| CA | 2426251 A1 * | 4/2002 |
| FR | 2 815 636 | 4/2002 |
| WO | WO 02 22735 | 3/2002 |

OTHER PUBLICATIONS

Liu et al. "Preparation and Spectroscopic Properties of Phenanthrene-Labeled SEBS Triblock Copolymers". *Macromolecules*, vol. 32, No. 12, pp. 3957-3963 (Apr. 27, 1999).
Al-Sabagh et al. "Water-based non-ionic polymeric surfactants as oil spill dispersants". *Journal of Chemical Technology and Biotechnology*, vol. 74, pp. 1075-1081 (May 22, 1999).
Qunitana et al. "Crystallization and thermal behavior of poly (vinylidene fluoride)/.Poly [styrene-b-(ethylene-co-butylene)-b-styrene] blends functionalized with succinic groups". *Journal of Polymer Science: Part B: Polymer Physics*, vol. 32, pp. 201-204 (Mar. 11, 1993).
Lin et al. "Synthesis, characterization, and interfacial behaviors of poly(oxyethylene)-grafted SEBS copolymers". *Industrial & Engineering Chemistry Research*, vol. 39, No. 1, pp. 65-71 (Nov. 30, 1999).
Derwent Abstract, week 199347ndon: Derwent Publications Ltd., AN 1993-374751, JP 05-279623 A, (Nippon Steel Chem Co), abstract, (Oct. 1993).
Donatas Satas (Ed.) *Handbook of Pressure Sensitive Adhesive Technology, Second Edition*, Chapter 13, pp. 317 to 359 (Apr. 1989). [Year of publication is sufficiently earlier than the effective U.S. filing date and any foreign priority date so that the particular month of publication is not an issue. MPEP 609.04(a).].

* cited by examiner

*Primary Examiner*—Kriellion Sanders
(74) *Attorney, Agent, or Firm*—Merchant & Gould P.C.

(57) ABSTRACT

The present invention relates to novel hydrophilic adhesive compositions, characterised in that they comprise a thermoplastic elastomer of poly(styrene-olefin-styrene) block copolymer type, a tackifying product, a liquid plasticizer, water and un amphiphilic copolymer.

The invention also relates to the use of these novel hydrophilic adhesive compositions as adhesives for fixing any type of product, and notably products for medical, dermatological or cosmetological purposes, which come into contact with a wound, the skin or the mucous membranes.

27 Claims, No Drawings

HYDROPHILIC ADHESIVE COMPOSITIONS

The present invention relates to novel hydrophilic thermofusible adhesive compositions, characterised in that they comprise a thermoplastic elastomer of poly(styrene-olefin-styrene) block copolymer type, a tackifying product, a liquid plasticizer, water and an amphiphilic copolymer.

The invention also relates to the use of these novel hydrophilic adhesive compositions as adhesives for fixing any type of product and notably products for medical, dermatological or cosmetological purposes which come into contact with a wound, the skin or the mucous membranes.

The preparation of adhesive compositions based on a thermoplastic elastomer of poly(styrene-olefin-styrene) block copolymer type has been known for a long time.

Thus, pressure-sensitive adhesives are prepared from compositions which comprise a poly(styrene-olefin-styrene) block copolymer, a tackifying product, such as, for example, a tackifying resin and a liquid plasticizer, such as, for example, a plasticizing oil, as essential constituents.

Such compositions are thus defined in the <<Handbook of Pressure Sensitive Adhesive technology>> $2^{nd}$ Edition, edited by Donatas Satas in 1989, Chapter 13, pages 317 to 359.

These adhesives are used in very many industrial applications since they possess good mechanical properties (elasticity, cohesion, adhesiveness) that can be modulated by adjusting the nature (grade, viscosity, polarity, molar mass, etc . . . ) and the proportion of the three essential constituents which are the plasticizer, the tackifying product and the block copolymer.

The main drawback of the adhesive compositions hitherto known originate from their exclusively hydrophobic nature, which renders them incompatible with water or hydrophilic products.

It is known to render these formulations more hydrophilic by incorporating therein fillers, such as, for example, cellulose derivatives, such as sodium carboxymethylcellulose, but this complicates the preparation of them and increases the manufacturing costs of them.

Moreover, the incorporation of water with such compositions causes the swelling of the hydrophilic filler and the loss of the good mechanical properties of the composition, such as its adhesiveness and its cohesion.

Today, there does not therefore exist a stable adhesive composition which can contain water, even in a low amount.

It is furthermore known within the context of a use on the skin, a wound or the mucous membranes, which constitute specific supports, that an adhesive must fulfil complex demands, and particularly it must have an acceptable appearance for the user, it must not lead to problems of tolerance during its use, nor cause pain or leave traces upon removal, and all this in preserving its adhesive, cohesive and elastic properties during its use.

Moreover, it is desirable to be able to incorporate in the adhesive, which then serves as a reservoir and as a delivery means, various compounds, such as, for example, pharmaceutical, cosmetological or dermatological actives.

Adhesives which are more particularly intended to be used on the skin, a wound or the mucous membranes, are thus described in the patent applications EP 758 009, EP 723 571 and EP 991 730.

However, the adhesives described in these patent applications still have many drawbacks and do not enable a certain number of problems to be solved satisfactorily.

Thus, in certain applications which necessitate the addition of liquid plasticizers an a relatively significant amount, very often oils, the adhesive does have a greasy or oily appearance from this, which lacks approval for the user. Furthermore, the migration of these plasticizers can lead to the appearance of marks or rings on the elements combined with the adhesive, such as, for example, the support, in the case of a patch, even to soiling the clothes in contact with this support.

Additionally, by virtue of their hydrophobic nature, the known adhesives have an occlusive effect which often leads to a maceration, which manifests itself by problems of tolerance during their use. This occlusive effect also manifests itself by the appearance of an aqueous interface which leads to a loss in the adhesion and to the correlative peeling off of the product, notably in case of sweating or during the production of exudates.

Finally, by virtue of this hydrophobic nature, it is very difficult, and sometimes even impossible, to incorporate hydrophilic actives in these compositions, the use of which can prove to be very useful, even indispensable in certain applications, such as, for example, an antiseptic, such as chlorhexidine digluconate, or plant extracts in the cosmetic field, or even electrolytes within the context of the preparation of electrodes.

The presence of water in the products intended to be applied on the skin, the mucous membranes or on a wound brings about a sensation of freshness, or of cold; enables the appearance of the final product to be improved, which appears less greasy; enables moisturising and softening the tissues by forming a moisturising film which promotes the hydro-physiological equilibrium of the skin, of a wound or of the mucous membranes, by thus avoiding the above-mentioned problems of tolerance.

It is for this reason that in the medical, dermatological or cosmetic fields, hydrogels are preferably used in contact with the skin, a wound or the mucous membranes. These hydrogels contain large amounts of water, often of the order of 30 to 80% by total weight with respect to the total weight of the hydrogel, and natural high-molecular weight polymers, such as, for example, polysaccharides, particularly glucomananes, galactomananes, carragheens; or synthetic polymers which are often cross-linked, in order to ensure the cohesion of the adhesive hydrogel, such as, for example, copolymers based on 2-acrylamido-2-methylpropane-sulfonic acid, which are marketed by the company LUBRIZOL under the designation AMPS®.

However, these hydrogels possess insufficient adhesion and cohesion properties. From this, they disintegrate and peel off easily, the surface of the adhesive is often altered or polluted by contact with the skin, a wound or the mucous membranes, and in general they are not repositionable once peeled off.

In contrast to the adhesives, and due to their hydrophilic nature, it is very difficult, even impossible to incorporate lipophilic or hydrophobic products with these hydrogels, and this consequently leads to the same problems of formulation as set forth above.

Finally, the implementation of the hydrogels is in general more delicate and more complex than that of the adhesives.

Taking into account this state of the art, it would therefore be desirable to have novel adhesive compositions at one's disposal which would combine the advantages of the known adhesives, namely to possess good properties of adhesion, of cohesion and of elasticity; and the advantages of the hydrogels, namely to possess a hydrophilic character and to contain water, even in very low amount.

Adhesives would thus be at one's disposal the hydrophilic character of which adhesives would lead to better performances and would open their field of use to new applications. Within the context of the applications for medical, cosmetic, pharmaceutical or dermatological purposes, in which there is a contact with the skin, a wound or the mucous membranes, an adhesive composition would be at one's disposal which is not very aggressive, which is well-tolerated, if necessary re-positionable, in which it would be possible to incorporate hydrophilic or lipophilic compounds, the use of which is pleasant, and susceptible to bringing about a sensation of freshness, which is simple to use, which is stable and which keeps its properties of adhesion and of cohesion during its use.

An aim of the present invention is novel, hydrophilic adhesive compositions which fulfil these aims and which notably enable the problems of incompatibility and of affinity of known adhesives with water and hydrophilic products, to be solved.

It has been discovered and this constitutes the basis of the present invention, that it was possible to render hydrophilic an adhesive composition based on a thermoplastic elastomer of poly(styrene-olefin-styrene) block copolymer type satisfactorily, and simple to use, by incorporating therein an amphiphilic copolymer of poly(styrene-ethylene-butylene-styrene) type which is grafted with hydrophilic groups. Such a composition can incorporate water or hydrophilic products, without loosing its basic properties.

Thus, according to a first aspect, the present application covers a hydrophilic adhesive composition, characterised in that it comprises:
- a thermoplastic elastomer, which is selected from the block copolymers poly(styrene-olefin-styrene), poly(styrene-olefin), and their mixtures,
- a tackifying product,
- a liquid plasticizer,
- water, and
- an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said copolymer ABA to be represented schematically by the following structure:

in which $R_1$ and $R_2$, which are identical or different, represent a hydrophilic group of average molar mass less than 10,000, which is selected from the following groups:

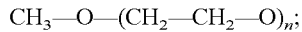

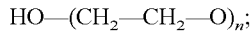

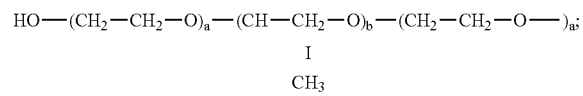

in which n, a and b represent an integer.

The hydrophilic adhesive compositions according to the invention thus possess a very wide range of properties which renders their exploitation possible in very many fields, and particularly in the preparation of products intended to be used in contact with the skin, a wound or the mucous membranes.

According to a second aspect, the present application covers the use of these novel hydrophilic adhesive compositions as adhesives for fixing any type of product, and notably products for medical, dermatological or cosmetological purposes which come into contact with a wound, the skin or the mucous membranes.

The detailed description that follows of the various constituents of the hydrophilic adhesive composition according to the invention will enable to better understanding the nature and the applications of this invention.

DESCRIPTION OF THE INVENTION

The amphiphilic copolymer which is used in the preparation of the hydrophilic adhesive compositions according to the invention is an ABA type block copolymer comprising two terminal thermoplastic poly(styrene) blocks A and one central elastomeric block B, in which this central block B is a poly(ethylene-butylene) sequence comprising grafted hydrophilic groups, it being possible for said amphiphilic copolymer ABA to be represented schematically by the following structure:

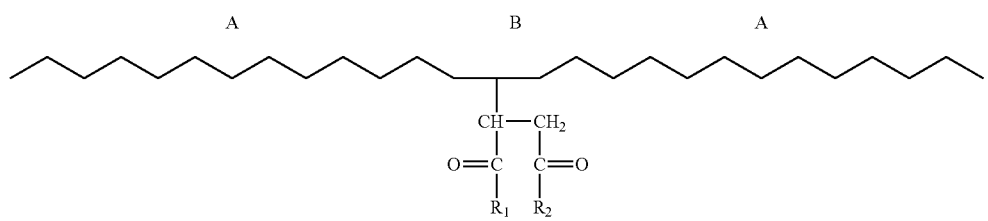

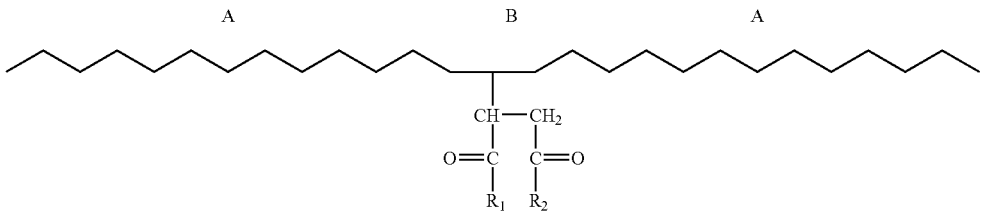

in which $R_1$ and $R_2$, which are identical or different, represent a hydrophilic group of average molar mass of less than 10,000, selected from the following groups:

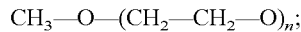

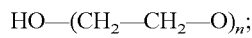

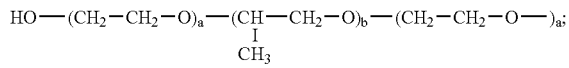

in which n, a and b represent an integer.

Advantageously, within the context of the present invention, the amphiphilic copolymers will be preferred in which $R_1$ and $R_2$ are identical.

Amongst these, the amphiphilic copolymers will preferably be used in which $R_1$ and $R_2$ represent a $CH_3$—O—$(CH_2—CH_2—O)_n$ group, particularly of average molar mass of between 1,000 and 8,000 and more particularly of average molar mass equal to 2,000 (i.e.=45).

These amphiphilic copolymers are obtained by grafting hydrophilic compounds onto a particular SEBS copolymer.

This particular copolymer comprises succinic anhydride functions which are distributed along the elastomeric poly(ethylene-butylene) chain, which are obtained by reaction of maleic anhydride with the poly(ethylene-butylene) sequence, and which will be called "maleated SEBS" in the following.

This maleated SEBS copolymer, which serves as the basis for the preparation of the amphiphilic copolymers according to the invention, can be represented schematically by the following formula:

A maleated SEBS marketed by the company SHELL under the designation Kraton G 1901® will be preferred as maleated SEBS, which contains 2% by weight of succinic anhydride functions fixed onto the elastomeric chain and 28% by weight of polystyrene.

It is these anhydride functions which will serve to graft the hydrophilic compounds by chemical reaction between the hydrophilic compound and the anhydride or its acid form.

According to the conditions of storage, and particularly according to the degree of drying of this maleated SEBS, a part of these succinic anhydride functions can in fact be present as their acid forms after opening of the anhydride in the presence of water. The reaction then takes place as well between the acid functions and the hydrophilic compound.

The hydrophilic compounds which are grafted onto the maleated SEBS are of 3 types:

A/Polyethyleneglycols, Hereinafter Referred to as the Abbreviation "PEGs"

These are hydrophilic, hygroscopic and heat-stable polymers. They are used in very many industrial fields. They are well-known to the person skilled in the art. They are short-chain polymers which possess hydroxyl functions on the extremities. Their average molar mass varies from 200 to 20,000.

Their composition corresponds to the following structure:

HO—$(CH_2—CH_2—O)_n$—H, in which n represents an integer.

Such products are for example marketed by the company Aldrich under the designation poly(ethylene glycol) followed by the average molar mass of the PEG considered, e.g. poly(ethyleneglycol) 2,000.

Within the context of the present invention, only amphiphilic copolymers in which the PEGs of average molar mass less than or equal to about 10,000 (n thus having

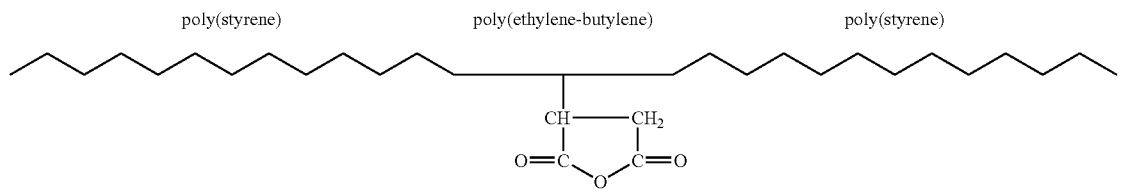

For reasons of simplicity, only one sole succinic anhydride group has been represented in this formula on the poly(ethylene-butylene) sequence. It is obvious that this sequence in reality comprises several succinic anhydride groups. This simplification has also been used in order to schematically represent the amphiphilic copolymers used within the context of the present invention.

at the maximum a value of 230) are used. Beyond, and the grafting reaction does in fact become difficult, even impossible.

Advantageously, the PEGs will be used which have an average molar mass of between 1,000 and 8,000, particularly the PEG which has an average molar mass of 2,000 (n=45).

B/Polyethyleneglycol Mono Methyl Ethers Hereinafter Referred to as the Abbreviation "PEGMEs"

These are also short-chain polymers which are used like the PEGs in very many fields and which are well-known to the person skilled in the art.

They have the following structure:

$CH_3—O—(CH_2—CH_2—O)_n—H$, in which n is an integer, and their average molar mass ranges from 200 to 20,000.

Such products are for example marketed by the company Aldrich under the designation poly(ethyleneglycol)methyl ether followed by the average molar mass of the PEGME considered, e.g. poly(ethyleneglycol)methylether 2,000.

Within the context of the present invention, amphiphilic copolymers are used in which, just as for the PEGs, only the PEGMEs of average molar mass less than or equal to about 10,000 (n having at the maximum a value of 230) are used.

Advantageously, the PEGMEs will be used which have an average molar mass of between 1,000 and 8,000, particularly the PEGME which has an average molar mass of 2,000 (n=45).

C/Polyethylene-polypropyleneglycol Copolymers

These are very well-known copolymers which will be designated hereinafter as the abbreviation PEO/PPO/PEO.

These are tri-block copolymers the central part of which is a polypropylene oxide block and the extremities of the polyethylene oxide blocks which have the following structure:

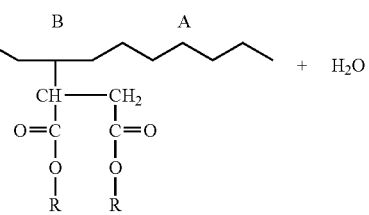

in which a and b are integers.

They are often designated as the general term "poloxamer".

Very many grades exist for these products which are characterised by the values a and b which define their average molar masses. The following can thus be cited:
poloxamer 124: a=12 b=20 average molar mass of between 2,090 and 2,360,
poloxamer 188: a=80 b=27 average molar mass of between 7,680 and 9,510,
poloxamer 407: a=101 b=56 average molar mass of between 9,840 and 14,600.

They are marketed for example by the company BASF under the designation Pluronic®.

Here, just as before, only the PEO/PPO/PEOs of average molar mass less than or equal to about 10,000 will be used.

Within the context of the present invention, a PEO/PPO/PEO will be preferred of molar mass neighbouring 2,000, such as, for example, the product marketed under the designation poly(ethyleneglycol)-block-poly(propyleneglycol)-block-poly(ethyleneglycol) 1900, by the company Aldrich, of average molar mass equal to 1,900.

The amphiphilic copolymers which can be used within the context of the present invention can be prepared easily by a reaction of esterification between the succinic anhydride functions of the maleated SEBS and the hydroxyl functions of the PEG, PEGME or PEO/PPO/PEO used.

The reaction of an alcohol with an anhydride function gives, reversibly, an ester. Within the context of the present invention, this esterification can be represented by the following simplified scheme:

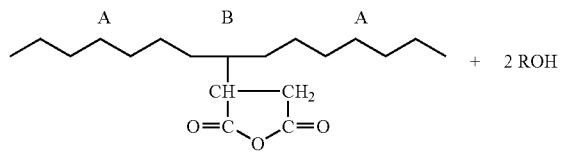

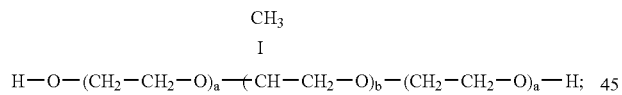

An excess of hydroxyl functions with respect to the anhydride functions is introduced, so as to promote the esterification reaction. Advantageously, the reaction is catalysed by an acid, and the water formed is removed by azeotropic distillation, in order to displace the equilibrium towards the grafted product. The reaction is preferably carried out under an inert atmosphere.

Thus, said amphiphilic copolymers are prepared according to a method in which a reaction of esterification is carried out between the succinic anhydride functions borne by the poly(ethylene-butylene) part of a poly(styrene)-poly (ethylene-butylene)-poly(styrene) copolymer (maleated SEBS) and the hydroxyl functions of a hydrophilic compound which is selected from polyethyleneglycols, (PEG), polyethyleneglycol mono methyl ethers (PEGME) and copolymers of polyethylene-propylene glycol (PEO/PPO/PEO) of average molar mass of less than or equal to 10,000, or their mixtures, preferably in the presence of an acid catalyst, by removing the water formed and with an excess of hydroxyl functions with respect to the succinic anhydride functions of the maleated SEBS.

More specifically, the synthetic method is the following:

The maleated SEBS is dissolved in the hot and with agitation, in a solvent, preferably toluene (at about 120° C., the reflux temperature of the solvent).

Apart, a solution is prepared of at least one hydrophilic compound (PEG, PEGME, PEO/PPO/PEO or their mixtures) by heating the latter compound(s) at its (their) melting temperature(s), with agitation, in a solvent, preferably toluene. Advantageously, an excess of hydrophilic compounds is used. The number of hydroxyl functions compared to the number of anhydride functions can thus vary from 2.5 to 20.

A catalytic amount (around a few drops) of acid, e.g. sulphuric acid, is added, and then the solution of hydrophilic compound(s) in the solvent prepared beforehand, to the solution of the maleated SEBS copolymer obtained beforehand, with agitation and keeping under reflux.

This mixture is agitated under azeotropic distillation, under reflux for 30 minutes to 5 hours according to the nature of the hydrophilic compound(s), until the complete reaction of esterification between the anhydride functions (or their eventual acid forms) of the succinic groups of the maleated SEBS and the hydroxyl functions of the hydrophilic compound(s). The extent of the reaction is tracked by using techniques which are well-known to the person skilled in the art, e.g. by infrared spectroscopy until the absorption peak of the carbonyls of the anhydride, i.e. 1,785 cm$^{-1}$, has disappeared.

The reaction mixture is then precipitated in the hot at about 90–100° C. in an adequate precipitation solvent, such as, for example, ethanol or an ethanol/water mixture, said precipitation solvent representing about 4 times the volume of the whole of the reaction solvents used.

After filtration, the residual solvents are removed from the amphiphilic SEBS copolymer obtained, by evaporation in the oven under vacuum at 40–50° C.

It is thus necessary to purify this latter product in order to remove the hydrophilic compound(s) PEG, PEGME or PEO/PPO/PEO used in excess, which is (are) still present.

The amphiphilic polymer obtained is therefore re-dissolved under agitation at about 90 to 110° C. in toluene, and the solution obtained is re-precipitated in the same solvent and the same volume as during the precipitation step carried out before at the end of the synthesis.

Similarly, the amphiphilic SEBS copolymer is recovered by filtration and is dried again in the oven under vacuum at 40–50° C.

This purification step is repeated until the total removal of the hydrophilic compound(s) by checking the absence of the peak of this (these) latter compound(s), in accordance with techniques which are well-known to the person skilled in the art, by gel permeation chromatography (GPC).

Within the context of the present invention, this amphiphilic copolymer will be used in the adhesive compositions at a concentration of the order of 0.05% to 20% by weight with respect to the total weight of the composition.

According to a preferred embodiment of the invention, an amphiphilic ABA type block copolymer will be used comprising two terminal thermoplastic poly(styrene) blocks A and one central elastomeric block B, in which this central block B is a poly(ethylene-butylene) sequence comprising grafted hydrophilic groups, it being possible for said amphiphilic copolymer ABA to be represented by the following structure:

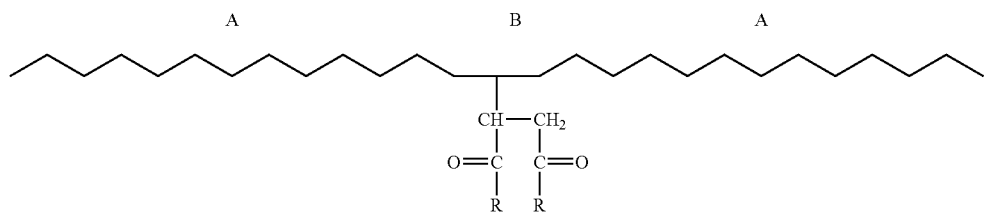

in which R represents a CH$_3$—O—(CH$_2$—CH$_2$—O)$_n$ group of average molar mass equal to 2000, i.e. n=45.

Such an amphiphilic copolymer will more particularly be preferred which has an average molar mass, measured by gel permeation chromatography, of the order of 50,000 daltons.

Preferably, this latter copolymer will then be used in the hydrophilic adhesive compositions at a concentration of the order of 0.05 to 20%, particularly 0.05 to 5% by weight with respect to the total weight of the composition.

The elastomers of (styrene-olefin-styrene) block copolymer type or (styrene-olefin) block copolymer type which can be used within the context of the present invention are those which are usually used by the person skilled in the art in the preparation of pressure-sensitive adhesives and reference in this respect may be made to the state of the art document mentioned above, and particularly to the book by Donatas Satas <<Handbook of Pressure Sensitive Technology>>.

These are therefore either ABA type triblock copolymers comprising two terminal thermoplastic styrene blocks A and one central elastomeric sequence B which is an olefin, or AB type diblock copolymers comprising a thermoplastic styrene block A and an elastomeric sequence B which is an olefin. The olefinic sequences B of these copolymers can be constituted of unsaturated olefins such as, for example, isoprene or butadiene, or of saturated olefins such as, for example, ethylene-butylene or ethylene-propylene.

It will be possible, within the context of the present invention, to use the whole of these products alone or as a mixture.

In the case of a mixture of ABA triblock copolymers and of AB diblock copolymers, it will be possible to employ commercial mixtures of ABA triblock copolymers and AB diblock copolymers which are already available, or to make a mixture in any proportion selected beforehand from two independent products.

The products having unsaturated central sequence are well-known to the person skilled in the art and are for example marketed by the company SHELL under the designation KRATON® D. The products marketed under the designations KRATON® D 1107 or KRATON® D 1161 can also be cited for the poly(styrene-isoprene-styrene) (abbreviated to SIS) copolymers and the product marketed under the designation KRATON® D 1102 can be cited for example for the poly(styrene-butadiene-styrene) copolymers. Other poly(styrene-isoprene-styrene) copolymers are also marketed by the company EXXON MOBIL CHEMICAL under the designation VECTOR®, such as, for example, the product marketed under the designation VECTOR® 4113. The product marketed by the company EXXON MOBIL CHEMICAL under the designation VECTOR® 4114, or the VECTOR® designated by the code DPX-565, in which B is isoprene, can be cited as examples of commercial mixtures of ABA triblock and AB diblock copolymers.

All these copolymers based on isoprene or butadiene in general have a styrene content of between 10 and 52% by weight with respect to the total weight of said copolymer.

Within the context of the present invention, triblock poly(styrene-isoprene-styrene) block copolymers will be preferred having a styrene content of between 14 and 30% by weight with respect to the weight of said SIS. The product marketed by the company SHELL under the designation KRATON® D 1161 will more particularly be preferred as poly(styrene-isoprene-styrene) triblocks block copolymer, and the product VECTORE DPX-565, marketed by the company EXXON MOBIL CHEMICAL, as mixture of poly(styrene-isoprene-styrene) triblocks block copolymer and poly(styrene-isoprene) diblocks block copolymer.

The products having a saturated central sequence are also well-known to the person skilled in the art and are for example marketed by the company SHELL under the designation KRATON® G for the poly(styrene-ethylene-butylene-styrene) (abbreviated to SEBS) block copolymers such as, for example, the products marketed under the designations KRATON® G 1651 or KRATON® G 1654, or by the company KURARAY under the designation SEPTON® for the poly(styrene-ethylene-propylene-styrene) (abbreviated to SEPS) block copolymers.

The product the olefinic sequence of which is ethylene-butylene marketed by the company SHELL under the designation KRATON® G 1657 can be cited as an example of commercial mixtures of triblock-diblock copolymers.

The mixture of a triblock SEBS can be cited as an example of a particular triblock-diblock mixture that can be used within the context of the present invention, such as the product marketed by the company SHELL under the designation KRATON® G 1651, with a poly(styrene-olefin) diblock material such as the poly(styrene-ethylene-propylene) marketed by the company SHELL under the designation KRATON® G 1702.

Within the context of the present invention, SEBS or SEPS triblock copolymers will be preferred, particularly those having a styrene content of between 25 and 45% by weight with respect to the weight of said SEBS. The product marketed by the company SHELL under the designation KRATON® G 1651 will more particularly be preferred.

In general, the thermoplastic elastomer will be used according to the nature of the block copolymer, in an amount of the order of 2 to 20% by weight with respect to the total weight of the composition. Preferably, a thermoplastic elastomer will be used which has an average molar mass of greater than that of the amphiphilic copolymer, preferably of the order of 100,000 daltons. In this case, the latter thermoplastic elastomer will then preferably be used in an amount of the order of 5 to 15% by weight with respect to the total weight of the composition.

If necessary, it will be possible to add anti-oxidising agents to these block copolymers. The term "anti-oxidising agent" is understood here as meaning the compounds which are commonly used by the person skilled in the art for ensuring the stability of the compounds used in the formulation of the adhesive compositions, particularly the tackifying resins and the block copolymers, against oxygen, heat, ozone and ultraviolet radiations. One or more of these anti-oxidising agents can be used in combination.

Phenolic anti-oxidising agents, such as, for example, the products marketed by the company CIBA-GEIGY under the designations IRGANOX® 1010, IRGANOX® 565, IRGANOX® 1076, and sulphur-containing anti-oxidising agents, such as, for example, zinc dibutyldithiocarbamate, marketed by the company AKZO under the designation PERKACIT® ZDBC, can be cited as appropriate anti-oxidising agents.

Within the context of the present invention, the term "tackifying" product is understood as meaning any product which enables the composition to be rendered adhesive.

Given that the composition contains both a hydrophobic phase, that can be qualified as lipophilic or oily, and an aqueous phase, the composition can be envisaged to be rendered adhesive by incorporating a tackifying product in at least one of the two phases. It is thus advantageously possible to employ a tackifying product which is compatible with the oily phase, or a tackifying product which is compatible with the aqueous phase, or even, a group of two tackifying products, one lipophilic and one hydrophilic, one in each phase.

Within the context of the preparation of adhesive compositions which are intended to be applied on the skin, a wound or the mucous membranes, the presence of water and the possibility of using two very different types of tackifying products offer a wide range of solutions for the regulation, which is always problematic, of the bioadhesion, and in order to prevent, upon peeling off, the alteration of the upper layers of the epidermis, or the pollution, further to this peeling off, of the surface of the adhesive which often prevents it from being re-stuck on.

Within the context of the present invention, it will therefore be possible to use one or more tackifying products in a wide proportion of the order of 1 to 50% by weight with respect to the total weight of the composition as a function of the other elements of this latter composition in order to obtain the adhesive power sought after for the final composition. Preferably, a tackifying product or a group of tackifying products will be used in a proportion of 2 to 30% by weight with respect to the total weight of the composition.

Within the context of the use of 2 tackifying products, one which is compatible with the aqueous phase, and the other with the oily phase, the group of these latter tackifying products will preferably be used in a total proportion of the order of 8 to 25% and notably of 8 to 15% by weight with respect to the total weight of the composition, particularly a proportion of the order of 2 to 5% by weight of tackifying product which is compatible with the aqueous phase and of 8 to 12% by weight of tackifying product which is compatible with the oily phase, and for the latter, more particularly 10% of low molecular weight polybutene with respect to the total weight of the composition.

The tackifying products which are compatible with the oily phase which are susceptible in being used within the context of the present invention are those which are usually used by the person skilled in the art in the preparation of pressure-sensitive adhesives comprising elastomers, and particularly poly(styrene-olefin-styrene) block copolymers, and it will be possible for reference to be made in this respect to the documents of the state of the art mentioned above, in particular to the book by Donatas Satas.

Within the context of the present invention, these products are in general selected from tackifying resins, and low molecular weight polybutenes, or their mixtures.

Polyterpene or modified terpene resins, hydrogenated colophane resins, polymerised colophane resins, colophane ester resins, hydrocarbonated resins, cyclic aromatic and aliphatic resin mixtures, etc . . . or their mixtures, can be mentioned from the tackifying resins which are suitable according to the invention.

Such products are for example marketed by the company GOODYEAR under the designation WINGTACK®, particularly such as the synthetic resin formed from C5/C9 copolymers which is marketed under the designation WINGTACK® 86 or based on synthetic polyterpene which is marketed under the designation WINGTACK® 10. The resins which are marketed under the designation KRISTALEX® by the company Hercules, particularly such as the resin based on alpha-methylstyrene, KRISTALEX® 3085, can also be cited as an example.

Within the context of the present invention, the resins marketed by the company EXXON MOBIL CHEMICAL under the designation ESCOREZ®, and more particularly the synthetic resin marketed under the designation ESCOREZ® 5300, will be preferred.

Within the context of the present invention, these resins will preferably be used in a proportion of the order of 2 to 30% by weight with respect to the total weight of the composition as a function of the adhesive power sought after for the final composition. More particularly, a proportion of resins of 5 to 25% by weight with respect to the total weight of the composition will be used.

The products which are well-known to the person skilled in the art, which are for example marketed under the designation NAPVIS® by the company BP CHIMIE, can be cited as low molecular weight polybutenes which can be used as tackifying product of the oily phase.

Within the context of the present invention, the product marketed under the designation NAPVIS® 10 will more particularly be preferred. These polybutenes can be used alone or as a mixture. They will preferably be used in a proportion of 5 to 30% by weight with respect to the total weight of the composition, and more particularly of 8 to 15% by weight.

The tackifying products which are compatible with the aqueous phase which can be used within the context of the present invention are usually used by the person skilled in the art for increasing or conferring sticky properties in the presence of water. These are generally non-cross-linked hydrosoluble synthetic polymers, such as polyvinylpyrrolidone polymers or polyvinylpyrrolidone copolymers, such as, for example, the vinylpyrrolidone polymers marketed by the company BASF under the designation KOLLIDON®, such as the product KOLLIDON® 30, polymers or copolymers of poly(vinyl alcohol), acrylic polymers, particularly such as the polyacrylates marketed by the company BF GOODRICH under the designation CARBOPOL® or the hydrosoluble polyvinyl ether polymers, e.g. the product marketed by the company BASF under the designation LUTONAL® M40.

Within the context of the present invention, these hydrosoluble polymers will preferably be used in a proportion of the order of 1 to 30% by weight with respect to the total weight of the composition as a function of the adhesive power sought after for the final composition. More particularly, a proportion of hydrosoluble polymers will be used of the order of 2 to 20% by weight with respect to the total weight of the composition.

Within the context of the present invention, the term "liquid plasticizer" is understood as meaning plasticizers which are usually used by the person skilled in the art for the preparation of pressure-sensitive adhesives which comprise thermoplastic elastomers, in particular of poly(styrene-olefin-styrene) block copolymer type and which are products which enable their properties of stretching, flexibility, extrudability or implementation to be improved, and reference may be made in this respect to the prior art documents mentioned above.

These liquid plasticizers are compounds which are compatible with the central olefin sequence of the block copolymers used. Plasticizing oils are used very often as liquid plasticizer, and particularly mineral oils which are formed from compounds of paraffinic, naphthenic or aromatic nature, or their mixtures, in variable proportions.

The products marketed by the company SHELL under the designation ONDINA® and RISELLA® can thus be cited as examples of mineral oils for the mixtures based on naphthenic and paraffinic compounds, or under the designation CATENEX® for the mixtures based on naphthenic, aromatic and paraffinic compounds.

Within the context of the present invention, paraffin oils will be preferred, particularly the oil marketed by the company SHELL under the designation ONDINA® 15.

As liquid plasticizer, not a plasticizing oil, but synthetic products based on liquid mixtures of saturated hydrocarbons can also be used, such as, for example, the products marketed by the company TOTAL under the designation GEMSEAL®, particularly such as the product GEMSEAL® 60 which is an isoparaffinic mixture originating from a totally hydrogenated petroleum fraction.

Within the context of the preparation of a hydrophilic adhesive composition according to the invention, a concentration of liquid plasticizer will preferably be used of the order of 25 to 90% by weight with respect to the total weight of the composition, preferably 30 to 75% by weight with respect to the total weight of the hydrophilic adhesive composition.

Finally, the hydrophilic adhesive composition according to the invention comprises water. It will be possible to use any type of water according to the fields of application envisaged such as, for example, spring water, tap water, demineralised, purified, deionised, or sterilised water.

It will of course be possible to incorporate any adjuvant with this water which is useful for preserving these properties of purity or of sterility with time.

Similarly, according to the application sought after, it will be possible to introduce very low amounts of water of the order of 1% by weight with respect to the total weight of the composition or large amounts ranging up to 60% or more by weight with respect to the total weight of the composition.

Within the context of the present invention, adhesive compositions are preferred which comprise of the order of 1 to 50% by weight of water and more particularly 10 to 45% by weight with respect to the total weight of the composition.

A currently preferred composition of the invention comprises:

a. 2 to 20 parts by weight of a thermoplastic elastomer of average molar mass greater than or equal to 100,000 daltons, b. 30 to 75 parts by weight of liquid plasticizer, c. 2 to 30 parts by weight of tackifying product, d. 1 to 45 parts by weight of water, and e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said amphiphilic copolymer ABA to be represented schematically by the following structure:

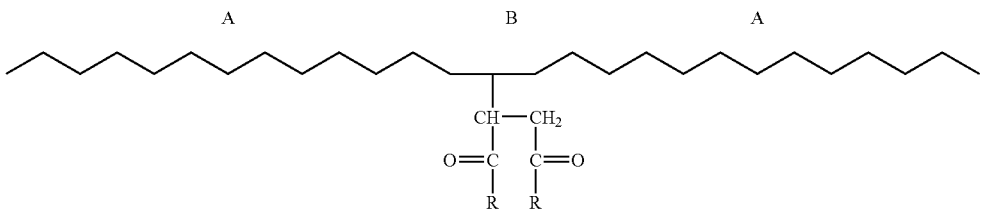

in which R represents a $CH_3-O-(CH_2-CH_2-O)_n$ group of average molar mass equal to 2,000 i.e. n=45, and which has an average molar mass measured by gel permeation chromatography of 50,000 daltons.

The following compositions will more particularly be preferred from the hydrophilic adhesive compositions included in this latter composition:

A composition which comprises:
a. 2 to 20 parts by weight of a thermoplastic elastomer of average molar mass greater than or equal to 100,000 daltons,
b. 30 to 75 parts by weight of liquid plasticizer,
c. 5 to 25 parts by weight of tackifying resin,
d. 10 to 40 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said amphiphilic copolymer ABA to be represented schematically by the following structure:

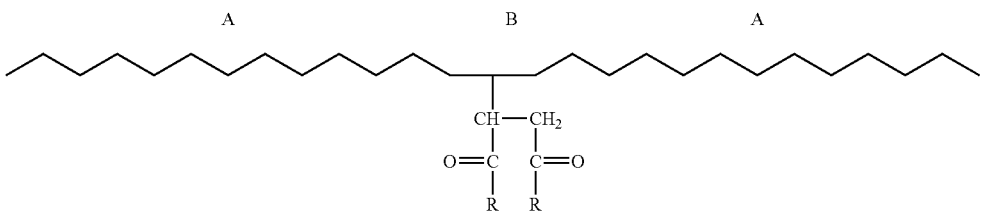

in which R represents a $CH_3-O-(CH_2-CH_2-O)_n$ group of average molar mass equal to 2,000 i.e. n=45 and which has an average molar mass measured by gel permeation chromatography of 50,000 daltons.

A composition which comprises:
a. 2 to 20 parts by weight of a thermoplastic elastomer of average molar mass greater than or equal to 100,000 daltons,
b. 30 to 75 parts by weight of liquid plasticizer,
c. 8 to 15 parts by weight of low molecular weight polybutene,
d. 10 to 40 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said amphiphilic copolymer ABA to be represented schematically by the following structure:

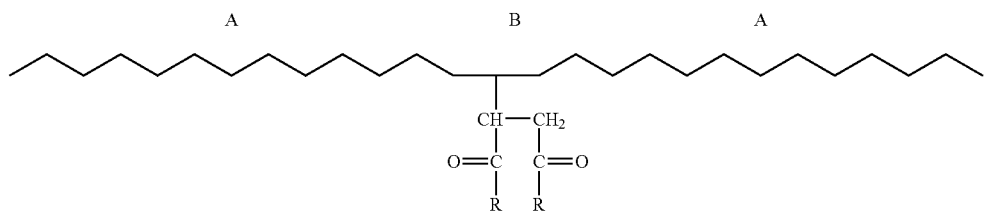

in which R represents a $CH_3-O-(CH_2-CH_2-O)_n$ group of average molar mass equal to 2,000 i.e. n=45 and which has an average molar mass measured by gel permeation chromatography of 50,000 daltons.

A composition which comprises:
a. 2 to 20 parts by weight of a thermoplastic elastomer of average molar mass greater than or equal to 100,000 daltons,
b. 30 to 75 parts by weight of liquid plasticizer,
c. 2 to 20 parts by weight of hydrosoluble polymer,
d. 10 to 40 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said amphiphilic copolymer ABA to be represented schematically by the following structure:

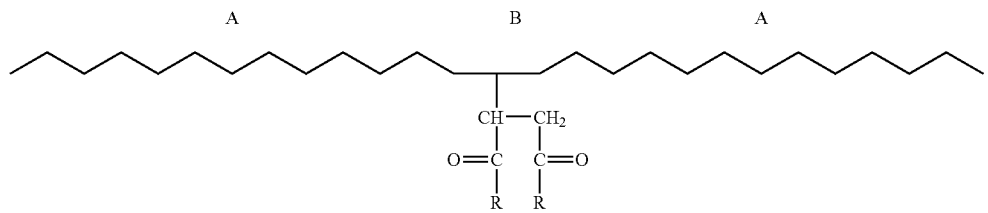

in which R represents a $CH_3-O-(CH_2-CH_2-O)_n$ of average molar mass equal to 2,000 i.e. n=45 and which has an average molar mass measured by gel permeation chromatography of 50,000 daltons.

A composition which comprises:
a. 2 to 20 parts by weight of a thermoplastic elastomer of average molar mass greater than or equal to 100,000 daltons,
b. 30 to 75 parts by weight of liquid plasticizer,
c. 8 to 15 parts by weight of a group of tackifying products which is constituted of a low molecular weight polybutene and of a hydrosoluble polymer and more particularly 10 parts by weight of low molecular weight polybutene and 2 to 5 parts de vinylpyrrolidone polymer,
d. 10 to 40 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, it being possible for said amphiphilic copolymer ABA to be represented schematically by the following structure:

in which R represents a $CH_3-O-(CH_2-CH_2-O)_n$ group of average molar mass equal to 2,000 i.e. n=45 and which has an average molar mass measured by gel permeation chromatography of 50,000 daltons.

Many fields exist in which the thermoplastic adhesive compositions according to the invention can be used as soon as the hydrophilic character enables an improvement to be provided to the adhesive.

In general, they present very many advantages and prove to be particularly useful every time that it is necessary to apply, for medical, dermatological, pharmaceutical or cosmetic purposes, a device on the skin, a wound or the mucous membranes, e.g. a dressing or a bandage for treating or protecting the skin, a wound, burns, a blister, deep, chronic or grave superficial dermo-epidermic lesions, for preparing a patch for the topical or systemic release of actives, or for the cleansing or the care of the skin, such as, for example, a scaling or anti-wrinkle product, for rendering an electrode adhesive or for fixing hygiene products intended to enter into contact with the skin, such as, for example, in nappies, for the preparation of adhesives for mammary prostheses, or in stoma for example for joints employed in ostomies.

By virtue of their aptitude to contain water or a hydrophilic active in a medium having a high hydrophobic content and vice versa, various compounds can be incorporated during the formulation of the hydrophilic adhesive composition, within the context of these applications. These compounds can be adjuvants or actives which are commonly used in the dermatological, cosmetic or pharmacological fields. Antioxidants, preservatives, perfumes, fillers, odour absorbers, colouring materials, UV filters, electrolytes for carrying current, pH regulators, bactericides, magnetisable particles, microcapsules or microspheres can thus be incorporated for example as adjuvants.

The amounts of these various adjuvants are those which are classically used in the field considered and for example 0.01 to 20% by weight with respect to the total weight of the composition. One or more actives selected from the following list can be incorporated as active agent: vitamins and their derivatives, glycerine, collagen, salicylic acid, aromatic essential oils, caffeine, anti-free radical actives, hydrating actives, depigmenting actives (such as kojic acid), liporegulating actives, anti-acne actives, anti-ageing actives,

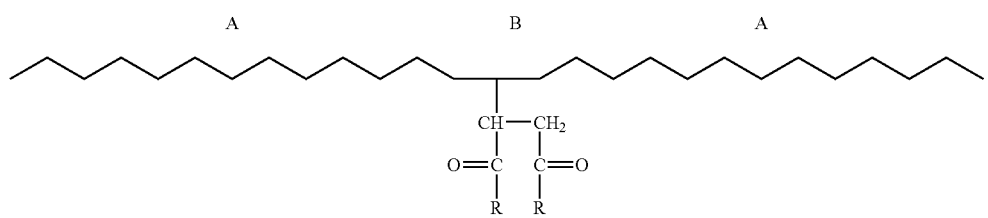

softening actives, decongesting actives, anti-wrinkle actives, refreshing actives, keratolitic agents and healing accelerating agents, vascular protecting agents, anti-bacterial agents such as sulfadiazine silver, anti-fungal agents, antiperspirant agents, deodorant agents, skin conditioning agents, anaesthetising compounds, immunomodulators, nourishing agents, plant extracts such as, for example, green tea, Arnica, hamamelis . . . , trace elements, local anaesthetics, anti-inflammatories, hormones, menthol, retinoids, DHEA, extracts of algae, of fungi, of yeast, of bacteria, hydrolysed, partially hydrolysed or non-hydrolysed proteins. This list is of course non-limiting.

The active(s) can for example be present at a concentration in the range of 0.01 to 20%, preferably 0.1 to 5%, better 0.5 to 3% of the total weight of the composition.

These adjuvants or these actives, according to their nature, can be introduced into the hydrophobic and lipophilic phase or into the aqueous phase. Of course, the person skilled in the art will take care to select the eventual additional actives or adjuvants and/or their amount such that the advantageous properties of cohesion, and of elasticity of the hydrophilic thermoplastic adhesive according to the invention not be or substantially not be altered by the addition envisaged.

Within the context of the preparation of products for medical, dermatological or cosmetic purposes such as, for example, patches, dressings, electrodes . . . , the hydrophilic adhesive layer which serves as a reservoir of actives or of adjuvants is in general combined with a support.

Given that the adhesive composition is, in this case the coating of the hydrophilic adhesive composition is carried out onto an adequate support of desired grammage, according to the technique which is well-known to the person skilled in the art, designated under the name "hot melt".

The choice of the support is made as a function of the properties which are required (waterproofness, elasticity, etc.) according to the type of product and the application sought after.

It can be presented as a film of variable thickness of 5 to 150 μm or as a non-woven, or a foam having a thickness of 10 to 500 μm. These supports based on synthetic or natural materials are those which are generally used by the person skilled in the art in the field of the applications mentioned above.

Polyethylene foams, polyurethane foams, PVC foams, polypropylene, polyamide, or polyester non-wovens, or complexes made based on a film and on a non-woven, etc. can thus be cited.

Practically, it will be possible for the surface of the hydrophilic adhesive composition which is not linked to the support to be covered with a protective layer or film which can be peeled off before use of the product. It will be possible for the assembly thus formed to be itself packaged in a waterproof protection made for example by means of polyethylene-aluminium complexes or in blisters.

The characteristics and applications of the invention will be better understood upon reading the following description of Examples of embodiments. The whole of these elements is of course in no way limiting, but is given solely as an illustration.

For reasons of simplicity, an example of synthesis of a representative amphiphilic copolymer will be given which will be used in all the adhesive compositions given as Examples which follow.

The method of synthesis of this copolymer is described in the Preparation I below.

A reactor equipped with a condenser, equipped with a drier, a sieve linked to the vacuum and to nitrogen if the reaction is carried out under an inert atmosphere, and a Dean-Stark, for removing the water formed by azeotropic distillation, are used in order to carry out the synthesis of this latter copolymer.

Preparation I 150 ml of toluene are introduced under nitrogen in a reactor. 20 g of Kraton G 1901® (maleated SEBS copolymer), marketed by the company SHELL, are added. Heat is given under reflux (about 110° C.) under agitation until total dissolution of the maleated SEBS copolymer. A solution of PEGME of molar mass 2,000, marketed by the company Aldrich under the designation poly(ethyleneglycol)methyl-ether 2000, is prepared apart. 32.32 g of PEGME 2000 are thus dissolved under agitation by heating at its melting temperature in 100 ml of toluene. About 20 drops of sulphuric acid are added to the solution of maleated SEBS copolymer obtained beforehand, still under agitation and under reflux. The solution of PEGME 2000 in toluene prepared beforehand is then added, still under agitation and under reflux. Thus, in this case, there are 4 hydroxyl functions for each anhydride function. The mixture obtained is kept agitated under reflux until the completion of the reaction of esterification, i.e. here about 30 to 40 minutes. The solution is then precipitated in the hot, at about 90 to 100° C., in 1.5 l of a 50/50 water-ethanol mixture. After filtration, the residual solvents are removed from the precipitate obtained by evaporation in the oven under vacuum at 40–50° C. It is necessary to remove the excess PEGME 2000 which has not reacted during the synthesis, in order to purify the amphiphilic polymer obtained. For this, the amphiphilic polymer is re-dissolved in the hot at about 90–100° C., with agitation, in 100 to 150 ml of toluene, and the solution obtained is again precipitated in 1.5 litres of a 50/50 water/ethanol mixture. After filtration, the recovered precipitate is dried under vacuum at 40–50° C. This purification step is repeated (re-dissolution-precipitation and drying under vacuum) until the PEGME 2000 is totally removed. An amphiphilic copolymer is thus obtained in which $R_1$ and $R_2$ represent a $CH_3$—O—$(CH_2$—$CH_2$—O—$)_n$ group in which n=45 which has an average molar mass of the order of 50,000 daltons, measured by gel permeation chromatography, with tetrahydrofuran as solvent, at a rate of 1 ml per minute, on a column marketed by the company WATERS under the designation STYRAGEL HR4, and with a refractive index detector.

EXAMPLES OF COMPOSITIONS ACCORDING TO THE INVENTION

Several adhesive compositions according to the invention have then been prepared:

1) Adhesive Compositions in which the Tackifier is a Resin

They are prepared according to the following preparative method:

The mixture of the various constituents is made in a closed reactor, heated to a temperature which ranges between 100 and 130° C., according to the nature of the thermoplastic elastomer, so as to melt the latter elastomer.

The agitation is made by virtue of a mixer equipped with a deflocculating helix at a speed of about 500 rpm.

Firstly, the amphiphilic copolymer, the water, the liquid plasticizer (a mineral oil in the following Examples) and all the other compounds, actives or adjuvants, which are not susceptible to being degraded at this temperature, except the tackifying product, which is here a tackifying resin, and the thermoplastic elastomer, are introduced into the reactor heated between about 100 and 130° C. The mixture thus formed is then agitated continuously until a homogeneous mixture is obtained.

Secondly, the tackifying resin is then introduced, keeping at the same temperature, and agitation is continued until a homogeneous mixture is obtained.

The thermoplastic elastomer is then incorporated into this mixture and agitation is continued keeping between 100 to 130° C., until a homogeneous mixture is obtained. If necessary, the thermoplastic elastomer can be mixed and melted with a small part of the liquid plasticizer before incorporation, in order to facilitate its homogenisation with the preceding mixture.

If necessary, the temperature is allowed to cool to less than 100° C. and any compound which is susceptible to being degraded at a higher temperature, such as, for example, liposoluble or hydrosoluble adjuvants and actives, such as a dry extract of Hamamelis in Example 2, is then incorporated, and agitation is done until a homogeneous mixture is obtained.

The constituents used for the preparation of the hydrophilic adhesive compositions described below in the Examples 1 to 4 are the following:

| | |
|---|---|
| PREPARATION I | amphiphilic copolymer |
| KRATON D 1161 ® | SIS marketed by the company SHELL |
| KRATON G 1651 ® | SEBS marketed by the company SHELL |
| ONDINA 15 ® | mineral oil marketed by the company SHELL |
| ESCOREZ 5300 ® | tackifying resin marketed by the company EXXON CHEMICAL |
| WATER | |
| METHYLPARABEN | hydrophobic preservative |
| PROPYLPARABEN | hydrophilic preservative |
| EXTRACT of *HAMAMELIS* | hydrophilic active marketed by the company SEPPIC |

The amounts of the various constituents of these hydrophilic adhesive compositions expressed in percentages by weight with respect to the total weight of the composition are grouped together in Table I.

TABLE I

| | EX. 1 | EX. 2 | EX. 3 | EX. 4 |
|---|---|---|---|---|
| PREPARATION I | 2.7 | 4 | 2 | 2 |
| KRATON G 1651 ® | 2.7 | | | |
| KRATON D 1161 ® | | 5 | 7 | 4 |
| ONDINA 15 ® | 32.1 | 46 | 43 | 35 |
| ESCOREZ 5300 ® | 15.7 | 6 | 12 | 7 |
| WATER | 46.8 | 38.6 | 36 | 52 |
| METHYLPARABEN | | 0.2 | | |
| PROPYLPARABEN | | 0.2 | | |
| EXTRACT Of *HAMAMELIS* | | 0.4 | | |

2) Adhesive Composition in which the Tackifier is a Hydrosoluble Polymer.

Example 5

In a closed, double-envelope reactor heated at a temperature which ranges between 90 and 100° C., the following are incorporated, successively, under agitation by virtue of a mixer equipped with a deflocculating helix, at a speed of about 500 to 800 rpm: 1 g of amphiphilic copolymer obtained according to the Preparation I, 29.4 g of water, 7.36 g of polyvinylpyrrolidone polymer marketed by the company BASF under the designation Kollidon® 30, 56.8 g of plasticizer (liquid mixture of saturated hydrocarbons) marketed by the company TOTAL under the designation GEMSEAL® 60, 0.2 g of hydrophobic preservative (Methylparaben) and 0.2 g of hydrophilic preservative (Propylparaben).

This agitation is maintained keeping at a temperature of between 90 and 100° C., until a homogeneous mixture is obtained.

5 g of VECTOR® DPX-565, mixture of triblocks copolymer (styrene-isoprene-styrene) and of diblocks copolymer (styrene-isoprene), marketed by the company EXXON MOBIL Chemical, are then introduced, keeping at a temperature of between 90 and 100° C. and under agitation. Agitation is continued keeping at the same temperature until a homogeneous mixture is obtained.

This mixture is the hydrophilic adhesive composition which is ready for use.

3) Adhesive Composition in which the Tackifier is a Low Molecular Weight Polybutene.

Example 6

In a closed, double-envelope reactor equipped with a mixer equipped with a deflocculating helix, heated at a temperature which ranges between 90 and 100° C., the following are incorporated successively: 55.6 g de GEMSEAL® 60 (liquid plasticizer), 10 g of low molecular weight polybutene marketed by the company BP Chemical under the designation NAPVIS® 10.

1 g of amphiphilic copolymer obtained according to the Preparation I, 23 g of water, 0.2 g of hydrophobic preservative (Methylparaben), 0.2 g of hydrophilic preservative (Propylparaben) are then introduced keeping at a temperature of between 90 and 100° C., and agitating at a speed of 800 rpm, until a homogeneous mixture is obtained.

10 g of VECTOR® DPX-565, are then incorporated, keeping at the same temperature, and agitation is kept at 800 rpm until a homogeneous mixture, which constitutes the hydrophilic adhesive composition, is obtained.

4) Hydrophilic Adhesive Composition in which a Tackifier is Incorporated in the Hydrophilic Phase and a Tackifier is Incorporated in the Hydrophobic Phase Example 7

55.6 g of GEMSEAL® 60 and 10 g of NAPVIS® 10 are introduced successively into a closed, double-envelope reactor equipped with a mixer equipped with a deflocculating helix, heated at a temperature of between 90 and 100° C., under agitation at a speed of about 800 rpm, until a homogeneous mixture is obtained. 1 g of amphiphilic copolymer obtained according to the Preparation I, 18.44 g of water, 4.56 g of Kollidon® 30, 0.2 g of Methylparaben and 0.2 g of Propylparaben are then introduced keeping at a temperature of between 90 and 100° C., and agitating at a speed of 800 rpm. Agitation is continued until a homogeneous mixture is obtained.

10 g of VECTOR® DPX-565 are then introduced and agitation is kept at the same speed, keeping at the same temperature, until a homogeneous mixture, which constitutes the hydrophilic adhesive composition, is obtained.

In the 3 preceding Examples, it will, as before, be possible to optionally mix the VECTOR® DPX-565 (thermoplastic elastomer) with a small amount of GEMSEAL® 60 (liquid plasticizer), taken from the total amount incorporated at the start of the preparative examples, before its incorporation in the mixture, in order to facilitate its homogenisation with the latter.

The hydrophilic adhesive compositions are then ready to be used for example incorporated in a product such as a patch.

In the case of Example 2, the adhesive composition has thus been deposited which contains a hydrophilic active and preservatives on a support, which is here a non-woven marketed by the company KURARAY, for the preparation of a patch product which can be used as a product for the care, the cleansing or the treatment of the skin, by virtue of its astringent, decongesting, calming and antibacterial properties of the extract of Hamamelis.

The analysis of Table I illustrates the originality of the compositions according to the present invention.

It is thus noted that it was possible to incorporate water in an amount ranging up to 52% in Example 4, in an adhesive composition.

Similarly, it was possible to incorporate a mixture of hydrophilic and hydrophobic adjuvants, the parabens, and a hydrophilic active, the extract of Hamamelis, in the Example 2.

Finally, when the product based on Hamamelis of Example 2 is applied on the skin, it is noted that it brings about a very pleasant sensation of freshness due to its relatively high water content (38.6%).

Similarly, Examples 5 to 7 illustrate the possibilities of preparing a hydrophilic adhesive composition (the percentage of water ranges from about 20 to 30%) by adjusting the addition of a tackifier in the hydrophilic phase (Example 5), in the hydrophobic phase (Example 6) or in both (Example 7).

The present invention thus appears to be particularly advantageous, insofar as it enables having for the first time in the state of the art hydrophilic adhesive compositions at one's disposal which enable pre-determined amounts of water or of hydrophilic compounds to be incorporated with compositions which possess good properties of adhesion, of cohesion and of elasticity, and offers many possibilities for regulating the adhesive properties of these compositions.

The compositions thus obtained can be used in a wide range of applications, particularly for the preparation of products for cosmetic, pharmaceutical, dermatological or medical usage, which are intended to be placed in contact with the skin.

The invention claimed is:

1. A hydrophilic adhesive composition, which comprises:
   a thermoplastic elastomer, which is selected from the group consisting of poly(styrene-olefin-styrene) block copolymers, poly(styrene-olefin) block copolymers and their mixtures,
   a tackifying product,
   a liquid plasticizer,
   water, and
   an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

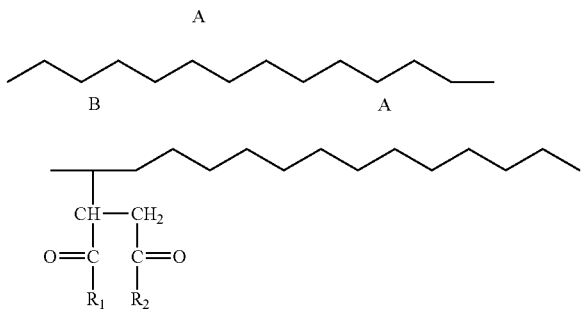

in which $R_1$ and $R_2$, which are identical or different, represent a hydrophilic group of average molar mass less than 10,000, selected from the group consisting of:

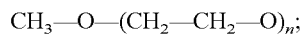

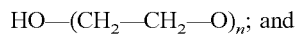

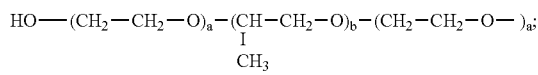

in which n, a and b represent an integer.

2. The hydrophilic adhesive composition according to claim 1, wherein the amphiphilic copolymer is an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

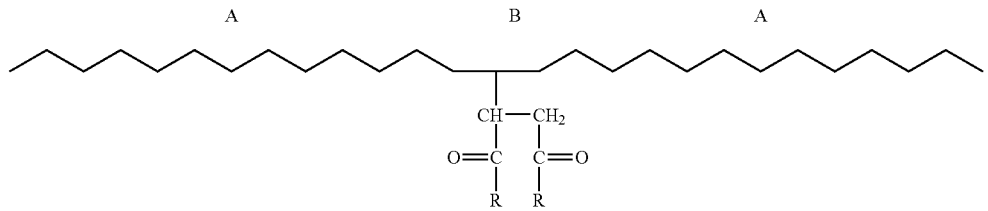

in which R represents a $CH_3$—O—$(CH_2CH_2$—O$)_n$ group of average molar mass of between 1,000 and 8,000 and n is an integer.

3. The hydrophilic adhesive composition according to claim 2, wherein the amphiphilic copolymer has an average molar mass measured by gel permeation chromatography of the order of 50,000 daltons.

4. The hydrophilic adhesive composition according to claim 1 which comprises 0.05 to 20% by weight of said amphiphilic copolymer with respect to the total weight of the composition.

5. The hydrophilic adhesive composition according to claim 1 which comprises 1 to 50% by weight of tackifying product with respect to the total weight of the hydrophilic adhesive composition.

6. The hydrophilic adhesive composition according to claim 5, wherein the tackifying product is compatible with the hydrophobic phase of the hydrophilic adhesive composition.

7. The hydrophilic adhesive composition according to claim 6, wherein the tackifying product is selected from the group consisting of tackifying resins, low molecular weight polybutenes and their mixtures.

8. The hydrophilic adhesive composition according to claim 7, wherein the tackifying product is a tackifying resin which is present in a proportion of 5 to 25% by weight with respect to the total weight of the hydrophilic adhesive composition.

9. The hydrophilic adhesive composition according to claim 7, wherein the tackifying product is a low molecular weight polybutene present in a proportion of 5 to 30% by weight with respect to the total weight of the hydrophilic adhesive composition.

10. The hydrophilic adhesive composition according to claim 5, wherein the tackifying product is compatible with the aqueous phase of the hydrophilic adhesive composition and is non-cross-linked synthetic water-soluble polymers.

11. The hydrophilic adhesive composition according to claim 10, which comprises 1 to 30% by weight of tackifying product with respect to the total weight of the composition.

12. The hydrophilic adhesive composition according to claim 1, wherein the liquid plasticizer is a plasticizing oil or a liquid mixture of saturated hydrocarbons which is compatible with the central olefinic sequence of the thermoplastic elastomer.

13. The hydrophilic adhesive composition according to claim 12, which comprises 20 to 90% by weight of liquid plasticizer with respect to the total weight of the composition.

14. The hydrophilic adhesive composition according to claim 1 wherein the thermoplastic elastomer is a mixture of poly(styrene-olefin-styrene) copolymer and of poly(styrene-olefin) copolymer.

15. The hydrophilic adhesive composition according to claim 1 wherein the thermoplastic elastomer is selected from the group consisting of poly(styrene-olefin-styrene) block copolymers, poly(styrene-olefin) block copolymers and their mixtures, and wherein the olefinic portion of the block copolyers of said thermoplastic elastomer is selected from the group consisting of isoprene, butadiene, ethylene-butylene and ethylene-propylene.

16. The hydrophilic adhesive composition according to claim 1 wherein the thermoplastic elastomer is present at a concentration of 2 to 20% by weight with respect to the total weight of the composition.

17. The hydrophilic adhesive composition according to claim 1 which comprises 1 to 50% by weight of water with respect to the total weight of the composition.

18. A hydrophilic adhesive composition which comprises:
a. 2 to 20 parts by weight of a thermoplastic elastomer of average molar mass greater than or equal to 100,000 daltons,
b. 30 to 75 parts by weight of liquid plasticizer,
c. 2 to 30 parts by weight of tackifying product,
d. 1 to 45 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

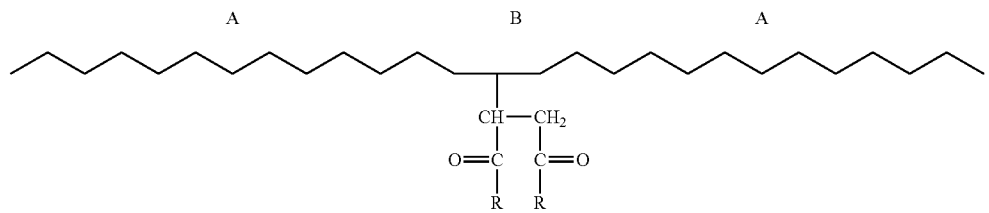

in which R represents a $CH_3$—O—$(CH_2$—$CH_2$—O$)_n$ group of average molar mass equal to 2,000, and n is 45, and which has an average molar mass measured by gel permeation chromatography of 50,000 daltons.

19. The hydrophilic adhesive composition according to claim 18, which comprises:
a. 2 to 20 parts by weight of a thermoplastic elastomer of average molar mass greater than or equal to 100,000 daltons,
b. 30 to 75 parts by weight of liquid plasticizer,
c. 5 to 25 parts by weight of tackifying resin,
d. 10 to 40 parts by weight of water, and
e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

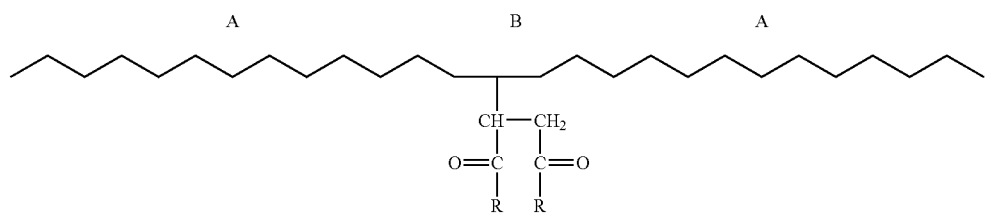

in which R represents a $CH_3-O-(CH_2-CH_2-O)_n$ group of average molar mass equal to 2,000, and n is 45, and which has an average molar mass measured by gel permeation chromatography of 50,000 daltons.

20. The hydrophilic adhesive composition according to claim 18, which comprises:
   a. 2 to 20 parts by weight of a thermoplastic elastomer of average molar mass greater than or equal to 100,000 daltons,
   b. 30 to 75 parts by weight of liquid plasticizer,
   c. 8 to 15 parts by weight of low molecular weight polybutene,
   d. 10 to 40 parts by weight of water, and
   e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented schematically by the following structure:

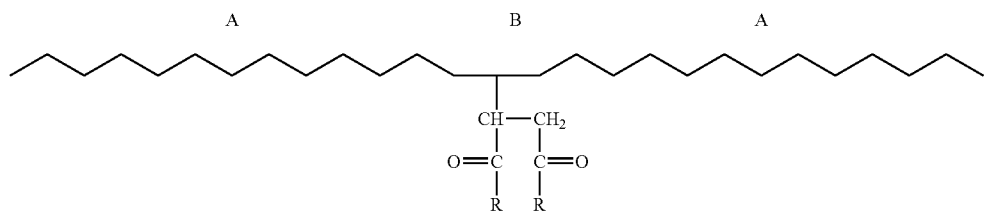

in which R represents a $CH_3-O-(CH_2-CH_2-O)_n$ group of average molar mass equal to 2,000, and n is 45, and which has an average molar mass measured by gel permeation chromatography of 50,000 daltons.

21. The hydrophilic adhesive composition according to claim 18, which comprises:
   a. 2 to 20 parts by weight of a thermoplastic elastomer of average molar mass greater than or equal to 100,000 daltons,
   b. 30 to 75 parts by weight of liquid plasticizer,
   c. 2 to 20 parts by weight of hydrosoluble polymer,
   d. 10 to 40 parts by weight of water, and
   e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

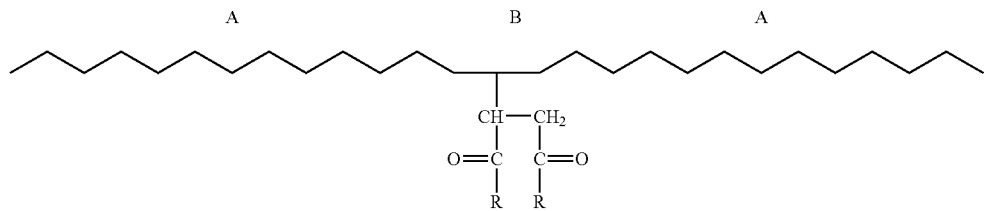

in which R represents a $CH_3-O-(CH_2-CH_2-O)_n$ group of average molar mass equal to 2,000, and n is 45, and which has an average molar mass measured by gel permeation chromatography of 50,000 daltons.

22. The hydrophilic adhesive composition according to claim 18, which comprises:
   a. 2 to 20 parts by weight of a thermoplastic elastomer of average molar mass greater than or equal to 100,000 daltons,
   b. 30 to 75 parts by weight of liquid plasticizer,
   c. 8 to 15 parts by weight of a group of tackifying products which is constituted of low molecular weight polybutene and hydrosoluble polymer,
   d. 10 to 40 parts by weight of water, and
   e. 0.05 to 5 parts by weight of an amphiphilic ABA type block copolymer comprising two terminal thermoplastic poly(styrene) blocks A and one central elastomeric block B in which the central block B is a poly(ethylene-butylene) sequence comprising grafted hydrophilic groups, wherein said amphiphilic copolymer ABA is represented by the following structure:

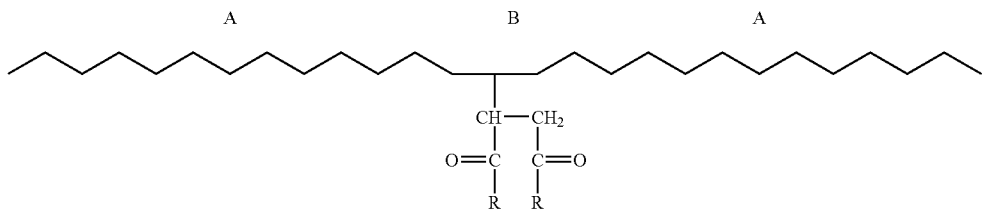

in which R represents a $CH_3$—O—$(CH_2$—$CH_2$—O$)_n$ group of average molar mass equal to 2,000, and n is 45, and which has an average molar mass measured by gel permeation chromatography of 50,000 daltons.

23. A product selected from the group consisting of medical, dermatological, cosmetological and pharmaceutical products which comprises a hydrophilic adhesive composition according to claim 1.

24. A product as claimed in claim 23, which is a product to be applied on the skin, a wound or the mucous membranes.

25. A product as claimed in claim 23 which is selected from the group consisting of a dressing for treating or protecting a wound, a blister, burns, or superficial dermo-epidermic lesions, a patch for delivering actives via the topical or systemic route, a product for the care, the cleansing or the protection of the skin or the mucous membranes, an electrode, and a product for stoma.

26. The hydrophilic adhesive composition according to claim 10, wherein the non-cross-linked synthetic water-soluble polymers is selected from the group consisting of polyvinylpyrrolidone polymers and polyvinylpyrrolidone copolymers.

27. The hydrophilic adhesive composition according to claim 16 wherein the thermoplastic elastomer has an average molar mass greater than that of the amphiphilic copolymer.

* * * * *